United States Patent
Subramaniyam

(10) Patent No.: US 10,711,204 B2
(45) Date of Patent: Jul. 14, 2020

(54) NITROGEN BASED HYDROGEN SULFIDE SCAVENGERS AND METHOD OF USE THEREOF

(71) Applicant: Dorf Ketal Chemicals (India) Private Limited, Mumbai (IN)

(72) Inventor: Mahesh Subramaniyam, Mumbai (IN)

(73) Assignee: Dorf Ketal Chemicals (India) Private Limited, Mumbai (IN)

( * ) Notice: Subject to any disclaimer, the term of this patent is extended or adjusted under 35 U.S.C. 154(b) by 119 days.

(21) Appl. No.: 16/068,018

(22) PCT Filed: Dec. 23, 2016

(86) PCT No.: PCT/IB2016/057994
§ 371 (c)(1),
(2) Date: Jul. 3, 2018

(87) PCT Pub. No.: WO2017/118894
PCT Pub. Date: Jul. 13, 2017

(65) Prior Publication Data
US 2019/0002768 A1  Jan. 3, 2019

(30) Foreign Application Priority Data
Jan. 8, 2016 (IN) .............................. 201621000847

(51) Int. Cl.
| | | |
|---|---|---|
| *B01D 53/52* | (2006.01) | |
| *C10G 21/20* | (2006.01) | |
| *C10G 29/20* | (2006.01) | |
| *C10L 3/10* | (2006.01) | |
| *C09K 8/532* | (2006.01) | |
| *C10L 1/14* | (2006.01) | |
| *C07C 7/152* | (2006.01) | |
| *C10G 21/16* | (2006.01) | |

(Continued)

(52) U.S. Cl.
CPC ............. *C10G 21/20* (2013.01); *B01D 53/52* (2013.01); *C07C 7/152* (2013.01); *C09K 8/532* (2013.01); *C10G 21/16* (2013.01); *C10G 29/20* (2013.01); *C10G 29/22* (2013.01); *C10L 1/14* (2013.01); *C10L 1/143* (2013.01); *C10L 1/18* (2013.01); *C10L 1/22* (2013.01); *C10L 3/103* (2013.01); *B01D 2252/20415* (2013.01); *B01D 2252/20431* (2013.01); *B01D 2252/20436* (2013.01); *B01D 2252/20489* (2013.01); *B01D 2252/504* (2013.01); *B01D 2256/24* (2013.01); *B01D 2257/306* (2013.01); *C09K 2208/20* (2013.01); *C10G 2300/207* (2013.01); *C10L 1/1832* (2013.01); *C10L 1/1852* (2013.01); *C10L 1/1985* (2013.01); *C10L 1/222* (2013.01); *C10L 1/2222* (2013.01); *C10L 1/2225* (2013.01); *C10L 1/232* (2013.01); *C10L 1/238* (2013.01); *C10L 2200/043* (2013.01); *C10L 2230/02* (2013.01); *C10L 2290/544* (2013.01); *C10L 2290/545* (2013.01)

(58) Field of Classification Search
CPC ................................ B01D 53/52; C10G 21/20
See application file for complete search history.

(56) References Cited

U.S. PATENT DOCUMENTS

| | | | | |
|---|---|---|---|---|
| 4,647,397 A | * | 3/1987 | Starkston | ............... C01B 17/167 |
| | | | | 252/189 |
| 5,698,171 A | * | 12/1997 | Trauffer | .................. B01D 53/48 |
| | | | | 423/220 |

(Continued)

FOREIGN PATENT DOCUMENTS

| | | |
|---|---|---|
| CN | 102698576 A | 10/2012 |
| CN | 104560252 A | 4/2015 |

(Continued)

OTHER PUBLICATIONS

Foreign communication from the priority International Application No. PCT/IB2016/057994, International Search Report and Written Opinion, dated Mar. 9, 2017, 10 pages.

(Continued)

*Primary Examiner* — Ellen M McAvoy
(74) *Attorney, Agent, or Firm* — Conley Rose, P.C.; Rodney B. Carroll

(57) ABSTRACT

The present invention relates to a hydrogen sulphide scavenging additive composition for scavenging hydrogen sulphide including sulfur containing compounds and mercaptans, particularly for scavenging hydrogen sulfide in hydrocarbons, wherein the additive composition comprises substantially reduced amount of nitrogen based hydrogen sulfide scavengers, and is also required in substantially reduced amount, and wherein the additive composition scavenges the sulfur containing compounds not only at room temperature, but also at higher temperatures, and comprises at least a combination of: (A) at least one nitrogen based hydrogen sulfide scavenger; and (B) at least one aliphatic tertiary amine, wherein the nitrogen based hydrogen sulfide scavenger comprises triazine based hydrogen sulfide scavenger. In one embodiment, it also relates to a method for scavenging hydrogen sulfide in hydrocarbons, and in another embodiment it relates to a method of using an additive composition of the present invention for scavenging hydrogen sulfide in hydrocarbons. In yet another embodiment, it relates to a composition comprising (i) a hydrocarbon and (ii) a hydrogen sulfide scavenging additive composition for scavenging hydrogen sulfide in hydrocarbons.

12 Claims, No Drawings

(51) Int. Cl.
*C10G 29/22* (2006.01)
*C10L 1/18* (2006.01)
*C10L 1/22* (2006.01)
*C10L 1/183* (2006.01)
*C10L 1/232* (2006.01)
*C10L 1/198* (2006.01)
*C10L 1/222* (2006.01)
*C10L 1/238* (2006.01)
*C10L 1/185* (2006.01)

(56) References Cited

U.S. PATENT DOCUMENTS

| | | | | |
|---|---|---|---|---|
| 8,663,457 | B2* | 3/2014 | Kaplan | C10G 29/20 |
| | | | | 208/207 |
| 10,196,343 | B2* | 2/2019 | Harrington | C10G 29/20 |
| 10,407,626 | B2* | 9/2019 | Rana | C10G 29/22 |
| 10,493,396 | B2* | 12/2019 | Subramaniyam | C08K 3/24 |
| 2004/0096382 | A1 | 5/2004 | Smith et al. | |
| 2011/0220551 | A1 | 9/2011 | Taylor | |
| 2013/0172623 | A1* | 7/2013 | Kaplan | C10G 29/24 |
| | | | | 564/471 |
| 2014/0171721 | A1 | 6/2014 | Bertrand, III | |
| 2016/0312141 | A1* | 10/2016 | Rana | C10L 3/103 |

FOREIGN PATENT DOCUMENTS

| | | |
|---|---|---|
| IN | 201621000847 | 1/2016 |
| RU | 2453582 C1 | 6/2012 |
| WO | 9007467 | 7/1990 |
| WO | 2009127604 A2 | 10/2009 |
| WO | 2017118894 A1 | 7/2017 |

OTHER PUBLICATIONS

Foreign communication from the priority International Application No. PCT/IB2016/057994, International Preliminary Report on Patentability of the International Preliminary Examining Authority, dated Mar. 21, 2018, 17 pages.

* cited by examiner

NITROGEN BASED HYDROGEN SULFIDE SCAVENGERS AND METHOD OF USE THEREOF

CROSS REFERENCE TO RELATED APPLICATIONS

This application is a filing under 35 U.S.C. 371 of International Application No. PCT/IB2016/057994 filed Dec. 23, 2016, entitled "Nitrogen Based Hydrogen Sulfide Scavengers and Method of Use Thereof," which claims priority to Indian Patent Application No. 201621000847 filed Jan. 8, 2016, which applications are incorporated by reference herein in their entirety.

FIELD OF THE INVENTION

The present invention generally relates to nitrogen based hydrogen sulfide scavengers and method of use thereof, and a method for scavenging hydrogen sulfide from hydrocarbons including hydrocarbon streams.

Particularly, it relates to nitrogen based hydrogen sulfide scavengers including triazine based hydrogen sulfide scavengers and a method of use thereof, and a method for scavenging hydrogen sulfide from hydrocarbons including hydrocarbon streams.

BACKGROUND OF THE INVENTION

The toxicity of hydrogen sulfide in hydrocarbons or hydrocarbon streams is well known in the industry and considerable expense and efforts are expended annually to reduce its content to a safe level. Many regulations require pipeline gas to contain no more than four (4) ppm hydrogen sulfide.

In large production facilities, it is generally more economical to install a regenerative system for treating streams containing hydrogen sulphide. These systems typically employ a compound used in an absorption tower to contact the produced fluids and selectively absorb the hydrogen sulfide and possibly other toxic materials such as carbon dioxide and mercaptans. The absorption compound is then regenerated and reused in the system. Typical hydrogen sulfide absorption materials include alkanolamines, hindered amines, and the like, i.e. nitrogen containing compounds. However, such approach is not economically feasible for development stage of a field or in small producing fields.

The nitrogen containing compounds, such as triazine, particularly monoethanolamine triazine (herein after the 'monoethanolamine triazine' may be referred to as 'MEA Triazine' or 'MEAT'; and 'triazine' and 'monoethanolamine triazine' collectively may be referred to as 'triazines') are known as hydrogen sulfide scavengers (re PCT publication no. WO 90/07467; and US publication nos. US 2004/0096382 and US 2011/0220551).

However, use of triazines as hydrogen sulfide scavengers suffers from difficulties and problems. For example, triazines are not substantially effective for scavenging hydrogen sulfide in liquid hydrocarbon streams, and dry gas streams. Further, use of triazines may also result in scale formation particularly in sea water containing calcium ions and dissolved carbon dioxide. To overcome problem of scale formation, one has to flush an acid to remove the scales formed. Therefore, the industry aims to minimize the amount of nitrogen based hydrogen sulfide scavengers, i.e. triazines.

NEED OF THE INVENTION

Accordingly, there is a need of an improved additive composition which, at least, comprises substantially reduced amount of nitrogen based hydrogen sulfide scavengers, and is also required in substantially reduced amount, and is suitable for scavenging sulfur containing compounds including, but not limited to hydrogen sulfide and mercaptans, particularly hydrogen sulfide in the hydrocarbons including hydrocarbon streams, and overcomes one or more of above-described problems of the prior art, and wherein the additive composition is capable of scavenging the sulfur containing compounds not only at room temperature, but also at higher temperatures.

Therefore, the present invention primarily aims at providing a solution to one or more of above-described existing industrial problems by providing an improved additive composition for scavenging sulfur containing compounds including, but not limited to hydrogen sulfide and mercaptans, particularly hydrogen sulfide in hydrocarbons including hydrocarbon streams without causing any problem, wherein the additive composition comprises substantially reduced amount of nitrogen based hydrogen sulfide scavengers, and is also required in substantially reduced amount, and wherein the additive composition is capable of scavenging the sulfur containing compounds not only at room temperature, but also at higher temperatures.

SUMMARY OF THE INVENTION

Accordingly, the main object of present invention is to provide an improved additive composition for scavenging sulfur containing compounds including, but not limited to hydrogen sulfide and mercaptans, particularly hydrogen sulfide in hydrocarbons including hydrocarbon streams and asphalt and which, at least, reduces the above-discussed problems of the prior art, wherein the additive composition comprises substantially reduced amount of nitrogen based hydrogen sulfide scavengers, i.e. triazines, and is also required in substantially reduced amount, and wherein the additive composition scavenges the sulfur containing compounds not only at room temperature, but also at higher temperatures.

This is also an object of present invention to provide a method for scavenging sulfur containing compounds including, but not limited to hydrogen sulfide and mercaptans, particularly hydrogen sulfide in hydrocarbons including hydrocarbon streams and asphalt by employing the additive composition of the present invention which comprises substantially reduced amount of nitrogen based hydrogen sulfide scavengers, i.e. triazines, and is also used in substantially reduced amount to scavenge the sulfur containing compounds, and wherein the additive composition scavenges the sulfur containing compounds not only at room temperature, but also at higher temperatures.

This is also an object of present invention to provide a method of using the additive composition of the present invention for scavenging sulfur containing compounds including, but not limited to hydrogen sulfide and mercaptans, particularly hydrogen sulfide in hydrocarbons including hydrocarbon streams and asphalt, wherein the additive composition comprises substantially reduced amounts of nitrogen based hydrogen sulfide scavengers, i.e. triazines, and thereby, makes the composition and its use economical, industrially feasible and convenient.

Other objects and advantages of present invention will become more apparent from the following description when read in conjunction with examples, which are not intended to limit scope of present invention.

DETAILED DESCRIPTION

With aim to overcome above-described problems of prior art and to achieve above-described objects of the invention, the inventor has found that when an hydrocarbon comprising sulfur containing compounds including, but not limited to hydrogen sulfide and mercaptans is treated with an additive composition comprising at least a combination of (a) at least one nitrogen based hydrogen sulfide scavenger; and (b) at least one aliphatic amine comprising at least one aliphatic tertiary amine, the sulfur containing compound including hydrogen sulfide is scavenged or removed.

With aim to overcome above-described problems of prior art and to achieve above-described objects of the invention, the inventor has also found that the scavenging of the sulfur containing compounds is achieved even when the additive composition of the present invention comprises a substantially reduced amount of nitrogen based hydrogen sulfide scavengers, i.e. triazines, and/or is used in a substantially reduced amount.

With aim to overcome above-described problems of prior art and to achieve above-described objects of the invention, the inventor has further found that the additive composition of the present invention scavenges the sulfur containing compounds not only at room temperature, but also at higher temperatures.

Accordingly, in main embodiment, the present invention, relates to a hydrogen sulfide scavenging additive composition for scavenging hydrogen sulfide in hydrocarbons comprising sulfur containing compounds including, but not limited to hydrogen sulfide and mercaptans, wherein said additive composition comprises at least a combination of (a) at least one nitrogen based hydrogen sulfide scavenger; and (b) at least one aliphatic amine comprising at least one aliphatic tertiary amine, wherein the nitrogen based hydrogen sulfide scavenger comprises triazine based hydrogen sulfide scavenger.

Accordingly, in another embodiment, the present invention, relates to a method for scavenging hydrogen sulfide in hydrocarbons comprising sulfur containing compounds including, but not limited to hydrogen sulfide and mercaptans, wherein the method comprises adding a hydrogen sulfide scavenging additive composition comprising at least a combination of (a) at least one nitrogen based hydrogen sulfide scavenger; and (b) at least one aliphatic amine comprising at least one aliphatic tertiary amine, wherein the nitrogen based hydrogen sulfide scavenger comprises triazine based hydrogen sulfide scavenger to the hydrocarbons.

Accordingly, in still another embodiment, the present invention, relates to a method of using a hydrogen sulfide scavenging additive composition comprising at least a combination of (a) at least one nitrogen based hydrogen sulfide scavenger; and (b) at least one aliphatic amine comprising at least one aliphatic tertiary amine, wherein the nitrogen based hydrogen sulfide scavenger comprises triazine based hydrogen sulfide scavenger for scavenging hydrogen sulfide in hydrocarbons comprising sulfur containing compounds including, but not limited to hydrogen sulfide and mercaptans, wherein the method comprises treating the hydrocarbon with the additive composition to scavenge the sulfur containing compounds including hydrogen sulfide.

Accordingly, in yet another embodiment, the present invention, relates to a composition for scavenging hydrogen sulfide in hydrocarbons comprising sulfur containing compounds including, but not limited to hydrogen sulfide and mercaptans, wherein the composition comprises at least a combination of (A) a hydrocarbon; and (B) a hydrogen sulfide scavenging additive composition, wherein the hydrogen sulfide scavenging additive composition comprises at least a combination of (a) at least one nitrogen based hydrogen sulfide scavenger; and (b) at least one aliphatic amine comprising at least one aliphatic tertiary amine, wherein the nitrogen based hydrogen sulfide scavenger comprises triazine based hydrogen sulfide scavenger.

In accordance with one of the preferred embodiments of the present invention, the nitrogen based hydrogen sulfide scavengers comprise triazine based hydrogen sulfide scavengers.

In accordance with one of the preferred embodiments of the present invention, the triazines comprise (or include) monoethanolamine triazine (MEAT) based hydrogen sulfide scavengers.

In accordance with one of the preferred embodiments of the present invention, the MEAT of any activity may be used.

In accordance with one of the preferred embodiments of the present invention, the MEAT may be of 32% activity or 50% activity or as may be supplied by its supplier/manufacturer.

In accordance with one of the preferred embodiments of the present invention, the aliphatic tertiary amine comprises tri-isopropanolamine (TIPA).

In accordance with one of the preferred embodiments of the present invention, the aliphatic tertiary amine comprises N,N,N',N'-Tetrakis (2-hydroxyethyl) ethylene-diamine (THEED).

In accordance with one of the preferred embodiments of the present invention, the aliphatic tertiary amine comprises ethylene oxide (EO) derivative of TIPA or ethoxylated TIPA (EO-TIPA).

In accordance with one of the preferred embodiments of the present invention, the aliphatic tertiary amine comprises propylene oxide (PO) derivative of TIPA or propoxylated TIPA (PO-TIPA).

In accordance with one of the preferred embodiments of the present invention, the aliphatic tertiary amine comprises ethylene oxide (EO) derivative of ethylene diamine or ethoxylated EDA (EO-EDA).

In accordance with one of the preferred embodiments of the present invention, the aliphatic tertiary amine comprises propylene oxide (PO) derivative of ethylene diamine or propoxylated EDA (PO-EDA).

In accordance with another preferred embodiment of the present invention, the aliphatic tertiary amine comprises tri-isopropanolamine (TIPA), N,N,N',N'-Tetrakis (2-hydroxyethyl) ethylene-diamine (THEED), ethylene oxide (EO) derivative of TIPA (EO-TIPA), propylene oxide (PO) derivative of TIPA (PO-TIPA), ethylene oxide (EO) derivative of ethylene diamine (EO-EDA), propylene oxide (PO) derivative of ethylene diamine (PO-EDA), or a mixture thereof.

In accordance with one of the preferred embodiments of the present invention, the mixture of aliphatic tertiary amines may be obtained by mixing one or more of the aliphatic tertiary amines of the present invention, i.e. TIPA, THEED, EO-TIPA, PO-TIPA, EO-EDA, and PO-EDA in any weight (or mole) ratio.

In accordance with one of the preferred embodiments of the present invention, the ethoxylated TIPA (EO-TIPA) may be obtained by reacting 1 mole of TIPA with at least 1 mole of ethylene oxide (EO).

For example, the ethoxylated TIPA may be obtained by reacting 1 mole of TIPA with 1 to 50 moles of ethylene oxide (EO).

For example, the ethoxylated TIPA may comprise:
TIPA ethoxyated by 5 moles of ethylene oxide (EO), herein after may be referred to as 'TIPA-5 mole EO' or 'TI5E';
TIPA ethoxyated by 10 moles of ethylene oxide (EO), herein after may be referred to as 'TIPA-10 mole EO' or 'TI10E';
TIPA ethoxyated by 15 moles of ethylene oxide (EO), herein after may be referred to as 'TIPA-15 mole EO' or 'TI15E';
TIPA ethoxyated by 20 moles of ethylene oxide (EO), herein after may be referred to as 'TIPA-20 mole EO' or 'TI20E';
TIPA ethoxyated by 25 moles of ethylene oxide (EO), herein after may be referred to as 'TIPA-25 mole EO' or 'TI25E';
TIPA ethoxyated by 30 moles of ethylene oxide (EO), herein after may be referred to as 'TIPA-30 mole EO' or 'TI30E'.

In accordance with one of the preferred embodiments of the present invention, the propoxylated TIPA (PO-TIPA) may be obtained by reacting 1 mole of TIPA with at least 1 mole of propylene oxide (PO).

For example, the propoxylated TIPA may be obtained by reacting 1 mole of TIPA with 1 to 50 moles of propylene oxide (PO).

For example, the propoxylated TIPA may comprise:
TIPA propoxylated by 5 moles of propylene oxide (PO), herein after may be referred to as 'TIPA-5 mole PO' or 'TI5P';
TIPA propoxylated by 10 moles of propylene oxide (PO), herein after may be referred to as 'TIPA-10 mole PO' or 'TI10P';
TIPA propoxylated by 15 moles of propylene oxide (PO), herein after may be referred to as 'TIPA-15 mole PO' or 'TI15P';
TIPA propoxylated by 20 moles of propylene oxide (PO), herein after may be referred to as 'TIPA-20 mole PO' or 'TI20P';
TIPA propoxylated by 25 moles of propylene oxide (PO), herein after may be referred to as 'TIPA-25 mole PO' or 'TI25P'.
TIPA propoxylated by 30 moles of propylene oxide (PO), herein after may be referred to as 'TIPA-30 mole PO' or 'TI30P'.

In accordance with one of the preferred embodiments of the present invention, the ethoxylated EDA (EO-EDA) may be obtained by reacting 1 mole of EDA with at least 1 mole of ethylene oxide (EO).

For example, the ethoxylated EDA may be obtained by reacting 1 mole of EDA with 1 to 50 moles of ethylene oxide (EO).

For example, the ethoxylated EDA may comprise:
EDA ethoxyated by 5 moles of ethylene oxide (EO), herein after may be referred to as 'EDA-5 mole EO' or 'EDA5E';
EDA ethoxyated by 10 moles of ethylene oxide (EO), herein after may be referred to as 'EDA-10 mole EO' or 'EDA10E';
EDA ethoxyated by 15 moles of ethylene oxide (EO), herein after may be referred to as 'EDA-15 mole EO' or 'EDA15E';
EDA ethoxyated by 20 moles of ethylene oxide (EO), herein after may be referred to as 'EDA-20 mole EO' or 'EDA20E';
EDA ethoxyated by 25 moles of ethylene oxide (EO), herein after may be referred to as 'EDA-25 mole EO' or 'EDA25E';
EDA ethoxyated by 30 moles of ethylene oxide (EO), herein after may be referred to as 'EDA-30 mole EO' or 'EDA30E'.

In accordance with one of the preferred embodiments of the present invention, the propoxylated EDA (PO-EDA) may be obtained by reacting 1 mole of EDA with at least 1 mole of propylene oxide (PO).

For example, the propoxylated EDA may be obtained by reacting 1 mole of EDA with 1 to 50 moles of propylene oxide (PO).

For example, the propoxylated EDA may comprise:
EDA propoxyated by 5 moles of propylene oxide (PO), herein after may be referred to as 'EDA-5 mole PO' or 'EDA5P';
EDA propoxyated by 10 moles of propylene oxide (PO), herein after may be referred to as 'EDA-10 mole PO' or 'EDA10P';
EDA propoxyated by 15 moles of propylene oxide (PO), herein after may be referred to as 'EDA-15 mole PO' or 'EDA15P';
EDA propoxyated by 20 moles of propylene oxide (PO), herein after may be referred to as 'EDA-20 mole PO' or 'EDA20P';
EDA propoxyated by 25 moles of propylene oxide (PO), herein after may be referred to as 'EDA-25 mole PO' or 'EDA25P';
EDA propoxyated by 30 moles of propylene oxide (PO), herein after may be referred to as 'EDA-30 mole PO' or 'EDA30P'.

With aim to overcome above-described problems of prior art and to achieve above-described objects of the invention, the inventor has also found that if the hydrogen sulfide scavenging additive composition of the present invention further comprises oxide derivative of nonyl phenol (NP), then the scavenging of the sulfur containing compounds is also achieved even when the additive composition of the present invention comprises a substantially reduced amount of nitrogen based hydrogen sulfide scavengers, i.e. triazines, and/or is used in a substantially reduced amount.

Therefore, in accordance with another embodiment of the present invention, the present additive composition may further comprise at least one oxide derivative of nonyl phenol (NP).

In accordance with one of the preferred embodiments of the present invention, the oxide derivative of nonyl phenol may comprise an ethylene oxide (EO) derivative of nonyl phenol (EO-NP), propylene oxide (PO) derivative of nonyl phenol (PO-NP), or a mixture thereof.

In accordance with one of the preferred embodiments of the present invention, the present composition does not comprise aliphatic secondary amine, aliphatic di-amine, aliphatic primary amine, aliphatic mono-amine, alkanolamine including monoalkanolamine, particularly including monoethanolamine (MEA), and triethanolamine (TEA).

In accordance with one of the preferred embodiments of the present invention, the hydrocarbon comprises (or includes) hydrocarbon stream including, but not limited to crude oil, fuel oil, sour gas, asphalts and refined products contained in storage tanks, vessels, and pipelines.

In accordance with one of the preferred embodiments of the present invention, the hydrogen sulfide containing compounds comprise (or include) sulfur containing compounds, or mercaptans, or a mixture thereof.

Accordingly, in accordance with one of the preferred embodiments of the present invention, in carrying out the method of scavenging or method of use of the present additive composition for scavenging the hydrogen sulfide in hydrocarbon including hydrocarbon stream, the scavenging additive composition is added to the hydrocarbon or gas stream or hydrocarbon stream in a concentration sufficient to substantially scavenge hydrogen sulfide therein.

In accordance with one of the preferred embodiments of the present invention, the present invention relates to a composition for scavenging hydrogen sulfide, wherein the composition comprises:
 (a) a hydrocarbon comprising sulfur containing compounds; and
 (b) a hydrogen sulfide scavenging additive composition;
  wherein the hydrogen sulfide scavenging additive composition comprises at least a combination of:
  (A) at least one nitrogen based hydrogen sulfide scavenger; and
  (B) at least one aliphatic tertiary amine,
   wherein the nitrogen based hydrogen sulfide scavenger comprises triazine based hydrogen sulfide scavenger; and
   wherein the aliphatic tertiary amine is the one as described herein.

In accordance with one of the preferred embodiments of the present invention, the present invention also relates to a hydrogen sulfide scavenging additive composition for scavenging hydrogen sulfide in hydrocarbon comprising sulfur containing compounds, wherein said additive composition comprises at least a combination of:
 (A) at least one nitrogen based hydrogen sulfide scavenger; and
 (B) at least one aliphatic tertiary amine,
  wherein the nitrogen based hydrogen sulfide scavenger comprises triazine based hydrogen sulfide scavenger;
  wherein the aliphatic tertiary amine comprises:
  (i) tri-isopropanolamine (TIPA);
  (ii) N,N,N',N'-Tetrakis (2-hydroxyethyl) ethylene-diamine (THEED);
  (iii) ethylene oxide derivative of TIPA (EO-TIPA);
  (iv) propylene oxide derivative of TIPA (PO-TIPA);
  (v) ethylene oxide derivative of ethylene diamine (EO-EDA);
  (vi) propylene oxide derivative of ethylene diamine (PO-EDA); or
  (vii) a mixture thereof.

In accordance with one of the preferred embodiments of the present invention, the present invention also relates to a hydrogen sulfide scavenging additive composition for scavenging hydrogen sulfide in hydrocarbon comprising sulfur containing compounds, wherein said additive composition does not comprise:
 a) monoethanol amine (MEA);
 b) diethanol amine (DEA); and
 c) triethanol amine (TEA).

In accordance with one of the embodiments of the present invention, it also relates to a method for scavenging hydrogen sulphide in hydrocarbon comprising sulfur containing compounds, wherein the method comprises contacting the hydrocarbon with the hydrogen sulfide scavenging additive composition of the present invention, wherein the hydrogen sulfide scavenging additive composition comprises at least a combination of:
 (A) at least one nitrogen based hydrogen sulfide scavenger; and
 (B) at least one aliphatic tertiary amine,
  wherein the nitrogen based hydrogen sulfide scavenger comprises triazine based hydrogen sulfide scavenger.

In accordance with one of the embodiments of the present invention, it also relates to a method of using the hydrogen sulfide scavenging additive composition of the present invention for scavenging hydrogen sulphide in hydrocarbon comprising sulfur containing compounds, wherein the method comprises adding to the hydrocarbon the hydrogen sulfide scavenging additive composition of the present invention, wherein the hydrogen sulfide scavenging additive composition comprises at least a combination of:
 (A) at least one nitrogen based hydrogen sulfide scavenger; and
 (B) at least one aliphatic tertiary amine,
  wherein the nitrogen based hydrogen sulfide scavenger comprises triazine based hydrogen sulfide scavenger.

In accordance with one of the preferred embodiments of the present invention, the hydrogen sulfide scavenging may be carried at a suitable temperature.

From the foregoing description and following supported examples, a reference to which is drawn here, it may be noted that:

Efficiency of nitrogen based hydrogen sulphide scavengers including triazine based hydrogen sulphide scavengers for scavenging hydrogen sulphide improves substantially on addition of the aliphatic tertiary amine of the present invention both at room temperature and at high temperature.

The improvement in efficiency of the nitrogen based hydrogen sulphide scavengers including triazine based hydrogen sulphide scavengers for hydrogen sulphide scavenging is substantially much higher on addition of the aliphatic tertiary amine of the present invention at high temperature as compared to that at room temperature.

The present invention is now described with the help of following examples, which are not intended to limit scope of present invention, but have been incorporated to illustrate advantages of present invention and best mode to perform it. The following examples also demonstrate surprising and unexpected effectiveness (synergistic effects) of the scavenging additive composition of present invention.

EXAMPLES

In the present examples, following abbreviations have been used:

MEAT is mono-ethanolamine triazine, it is taken in its two concentrations of 50% or 32%;
TIPA is tri-isopropanolamine;
EO-TIPA is ethylene oxide (EO) derivative of TIPA;
PO-TIPA is propylene oxide (PO) derivative of TIPA;
THEED is N,N,N',N'-Tetrakis (2-hydroxyethyl) ethylene-diamine;
EDA is ethylene diamine;
EO-EDA is ethylene oxide (EO) derivative of EDA;
PO-EDA is propylene oxide (PO) derivative of EDA;
NP is nonyl phenol;
EO-NP is ethylene oxide (EO) derivative of NP;
PO-NP is propylene oxide (PO) derivative of NP;

'TIPA-PO 4 mole' or may be written as 'TIPA-4 mole PO' or 'TI4P' is propylene oxide (PO) derivative of TIPA, and is obtained by reacting 1 mole of TIPA with 4 moles of propylene oxide (PO);

'TIPA-PO 8 mole' or may be written as 'TIPA-8 mole PO' or 'TI8P' is propylene oxide (PO) derivative of TIPA, and is obtained by reacting 1 mole of TIPA with 8 moles of propylene oxide (PO);

'TIPA-PO 10 mole' or may be written as 'TIPA-10 mole PO' or 'TI10P' is propylene oxide (PO) derivative of TIPA, and is obtained by reacting 1 mole of TIPA with 10 moles of propylene oxide (PO);

'TIPA-PO 16 mole' or may be written as 'TIPA-16 mole PO' or 'TI16P' is propylene oxide (PO) derivative of TIPA, and is obtained by reacting 1 mole of TIPA with 16 moles of propylene oxide (PO);

'TIPA-PO 20 mole' or may be written as 'TIPA-20 mole PO' or 'TI20P' is propylene oxide (PO) derivative of TIPA, and is obtained by reacting 1 mole of TIPA with 20 moles of propylene oxide (PO);

'TIPA-PO 25 mole' or may be written as 'TIPA-25 mole PO' or 'TI25P' is propylene oxide (PO) derivative of TIPA, and is obtained by reacting 1 mole of TIPA with 25 moles of propylene oxide (PO);

'TIPA-PO 30 mole' or may be written as 'TIPA-30 mole PO' or 'TI30P' is propylene oxide (PO) derivative of TIPA, and is obtained by reacting 1 mole of TIPA with 30 moles of propylene oxide (PO);

'TIPA-EO 10 mole' or may be written as 'TIPA-10 mole EO' or 'TI10E' is ethylene oxide (EO) derivative of TIPA and is obtained by reacting 1 mole of TIPA with 10 moles of ethylene oxide (EO).

'TIPA-EO 15 mole' or may be written as 'TIPA-15 mole EO' or 'TI15E' is ethylene oxide (EO) derivative of TIPA and is obtained by reacting 1 mole of TIPA with 15 moles of ethylene oxide (EO).

'TIPA-EO 20 mole' or may be written as 'TIPA-20 mole EO' or 'TIDE' is ethylene oxide (EO) derivative of TIPA and is obtained by reacting 1 mole of TIPA with 20 moles of ethylene oxide (EO).

'TIPA-EO 20.8 mole' or may be written as 'TIPA-20.8 mole EO' or 'TI208E' is ethylene oxide (EO) derivative of TIPA and is obtained by reacting 1 mole of TIPA with 20.8 moles of ethylene oxide (EO).

'TIPA-EO 26 mole' or may be written as 'TIPA-26 mole EO' or 'TI26E' is ethylene oxide (EO) derivative of TIPA and is obtained by reacting 1 mole of TIPA with 26 moles of ethylene oxide (EO).

'NP-EO 16 mole' or may be written as 'NP-16 mole EO' or 'NP16E' is ethylene oxide (EO) derivative of nonyl phenol (NP) and is obtained by reacting 1 mole of nonyl phenol (NP) with 16 moles of ethylene oxide (EO).

'NP-EO 20 mole' or may be written as 'NP-20 mole EO' or 'NP20E' is ethylene oxide (EO) derivative of nonyl phenol (NP) and is obtained by reacting 1 mole of nonyl phenol (NP) with 20 moles of ethylene oxide (EO).

'NP-EO 40 mole' or may be written as 'NP-40 mole EO' or 'NP40E' is ethylene oxide (EO) derivative of nonyl phenol (NP) and is obtained by reacting 1 mole of nonyl phenol (NP) with 40 moles of ethylene oxide (EO).

'NP-PO 40 mole' or may be written as 'NP-40 mole PO' or 'NP40P' is propylene oxide (PO) derivative of nonyl phenol (NP) and is obtained by reacting 1 mole of nonyl phenol (NP) with 40 moles of propylene oxide (PO).

'EDA-PO 8 mole' or may be written as 'EDA-8 mole PO' or 'EDA8P' is propylene oxide (PO) derivative of ethylene diamine (EDA) and is obtained by reacting 1 mole of EDA with 8 moles of propylene oxide (PO).

'EDA-PO 16 mole' or may be written as 'EDA-16 mole PO' or 'EDA16P' is propylene oxide (PO) derivative of ethylene diamine (EDA) and is obtained by reacting 1 mole of EDA with 16 moles of propylene oxide (PO).

'EDA-PO 20 mole' or may be written as 'EDA-20 mole PO' or 'EDA20P' is propylene oxide (PO) derivative of ethylene diamine (EDA) and is obtained by reacting 1 mole of EDA with 20 moles of propylene oxide (PO).

'EDA-PO 25 mole' or may be written as 'EDA-25 mole PO' or 'EDA25P' is propylene oxide (PO) derivative of ethylene diamine (EDA) and is obtained by reacting 1 mole of EDA with 25 moles of propylene oxide (PO).

'EDA-PO 31 mole' or may be written as 'EDA-31 mole PO' or 'EDA31P' is propylene oxide (PO) derivative of ethylene diamine (EDA) and is obtained by reacting 1 mole of EDA with 31 moles of propylene oxide (PO).

Polypropylene glycol having molecular weight of about 400 Daltons (PPG400);

Polypropylene glycol having molecular weight of about 1000 Daltons (PPG1000);

Polypropylene glycol having molecular weight of about 2000 Daltons (PPG2000);

Polypropylene glycol having molecular weight of about 3000 Daltons (PPG3000);

Polypropylene glycol having molecular weight of about 4000 Daltons (PPG4000), which are polymers made from propylene oxide.

Polyethylene glycol having molecular weight of about 200 Daltons (PEG200);

Polyethylene glycol having molecular weight of about 400 Daltons (PEG400);

Polyethylene glycol having molecular weight of about 600 Daltons (PEG600).

which are polymers made from ethylene oxide.

One of ordinary skill in the art may calculate active content dosage and ratio of the components (ingredients) of the present composition as known in the art. For example, as follows:

| Additive | Dosage (in ppm) | Active dosage (in ppm) would be |
| --- | --- | --- |
| MEAT (32%) + TIPA-PO 30 mole in 90/10 weight ratio | 500 + 17.5 | 160 + 17.5 |

Total active dosage=160+17.5=177.5 ppm

MEAT contribution would be=160/177.5× 100=90.14%~90%;

TIPA-PO contribution would be=17.5/177.5× 100=9.86%~10%.

Therefore, the weight ratio of MEAT(32%) and 'TIPA-PO 30 mole' would be 90:10.

By applying the above method, one of ordinary skill in the art may calculate the weight ratio, as taken in the present examples from the ppm dosages thereof.

The average molecular weight of the additives used in the present examples may be calculated by using gel permeation chromatography (GPC) in Daltons. For example, the average molecular weight of some of the additive amines used in the present invention is as tabulated herein below merely for the sake of information without any intention to limit the scope thereof:

TABLE I

| Additive | Mol. Wt. (by GPC in Daltons) |
|---|---|
| TIPA as such | 193 |
| TIPA-PO, 30 mole | 2264 |
| EDA-PO, 16 mole | 1117 |
| TIPA-EO, 26 mole | 1328 |
| NP-PO, 40 mole | 1921 |
| NP-EO, 20 mole | 1193 |

The $H_2S$ was purged in 100 ml of kerosene till concentration of $H_2S$ vapor reaches to 2000 ppm in blank sample [Blank-I]. To the resulted solution, a dosage of the prior art additive consisting of triazine and the additive composition of the present invention as given in following tables was added and $H_2S$ scavenging capabilities in % efficiency were measured at 50° C. for 15 minutes. The residual H2S in vapor was detected by a gas detector tube (Unifos). The results are presented in the following tables.

The hydrogen sulphide scavenging efficiency of some of the individual amines was also measured for dosages of 10 ppm, 100 ppm and 200 ppm. It may be noted that in the compositions of the present examples, the amine was added in an amount of less than 50 ppm, therefore, these comparative tests with dosages of 10 ppm, 100 ppm and 200 ppm are sufficient to know whether the individual amine would have hydrogen sulphide scavenging efficiency or not. It was found that the individual amines do not have hydrogen sulphide scavenging efficiency.

TABLE II

| Amine | Dosage (in ppm) | Efficiency (in % at 50° C.) |
|---|---|---|
| TIPA | 50 | 5 |
| TIPA | 100 | 10 |
| TIPA | 200 | 12.5 |
| EDA | 50 | 10 |
| TIPA-PO, 25 mole | 50 | 10 |
| TIPA-PO, 30 mole | 50 | 10 |
| TIPA-PO, 30 mole | 100 | 10 |
| TIPA-PO, 30 mole | 200 | 15 |
| EDA-PO 16 mole | 100 | 7.5 |
| EDA-PO 16 mole | 200 | 12.5 |

Similarly, the hydrogen sulphide scavenging efficiency of MEAT of 32% activity and of 50% activity was also measured. It was found that the MEAT has hydrogen sulphide scavenging efficiency, but it was found to be substantially low.

TABLE III

| Dosage (in ppm) [MEAT] | MEAT (32% active) |
|---|---|
| 500 | 45.5 |
| 600 | 72.7 |
| 700 | 77.3 |
| 900 | 84.1 |

TABLE IV

| Additive | Dosage (ppm) as such | % Efficiency (RT, 26° C.) | % Efficiency (60° C.) | % Efficiency (80° C.) | % Efficiency (100° C.) |
|---|---|---|---|---|---|
| MEAT (50% active) | 50 | 25 | 15 | 11 | 5 |
| | 100 | 50 | 40 | 20 | 15 |
| | 200 | 65 | 50 | 30 | 20 |
| | 300 | 75 | 70 | 60 | 45 |

The hydrogen sulphide scavenging efficiency of the present compositions comprising combination of MEAT (50% active) and amines of the present invention was measured at various temperatures, i.e. at room temperature (26° C.), and at 60° C., 80° C. and 100° C., and has been presented in Table V. It has been found that the hydrogen sulphide scavenging efficiency of the MEAT surprising and unexpectedly improves on addition of amines of the present invention, thereby confirming the synergistic effect of the present compositions.

TABLE V

| Composition | Dosage (ppm) as such | % Efficiency (RT, 26° C.) | % Efficiency (60° C.) | % Efficiency (80° C.) | % Efficiency (100° C.) |
|---|---|---|---|---|---|
| Blank | — | — | — | — | — |
| MEAT | 50 | 25 | 15 | 11 | 5 |
|  | 100 | 50 | 40 | 20 | 15 |
|  | 200 | 65 | 50 | 30 | 20 |
|  | 300 | 75 | 70 | 60 | 45 |
| MEAT (50 ppm) + TIPA (5 ppm) | 50 + 2.5 | 35 | 45 | 65 | 69 |
|  | 100 + 5 | 60 | 75 | 85 | 90 |
| MEAT (50 ppm) + TIPA-10 mole EO (5 ppm) | 50 + 2.5 | 50 | 60 | 63 | 72 |
|  | 100 + 5 | 80 | 80 | 80 | 90 |
| MEAT (50 ppm) + TIPA-15 mole EO (5 ppm) + | 50 | 55 | 60 | 70 | 75 |
|  | 100 | 80 | 80 | 85 | 85 |
| MEAT (50 ppm) + TIPA-20.8 mole EO (5 ppm) | 50 | 60 | 65 | 75 | 80 |
|  | 100 | 85 | 85 | 90 | 90 |
| MEAT (50 ppm) + TIPA-26 mole EO (5 ppm) | 50 | 55 | 65 | 75 | 80 |
|  | 100 | 85 | 85 | 90 | 90 |
| MEAT (50 ppm) + TIPA-4 mole PO (5 ppm) | 50 + 2.4 | 30 | 40 | 65 | 74 |
|  | 100 + 5 | 55 | 70 | 90 | 90 |
| MEAT (50 ppm) + TIPA-4 mole PO (5 ppm) | 50 | 40 | 50 | 70 | 81 |
|  | 100 | 65 | 80 | 95 | 100 |
| MEAT (50 ppm) + TIPA-8 mole PO (5 ppm) | 50 + 2.5 | 60 | 75 | 85 | 98 |
|  | 100 + 5 | 70 | 90 | 100 | 100 |

TABLE V-continued

| Composition | Dosage (ppm) as such | % Efficiency (RT, 26° C.) | % Efficiency (60° C.) | % Efficiency (80° C.) | % Efficiency (100° C.) |
|---|---|---|---|---|---|
| MEAT (50 ppm) + TIPA-10 mole PO (5 ppm) | 50 | 65 | 70 | 85 | 98 |
|  | 100 | 70 | 85 | 100 | 100 |
| MEAT (50 ppm) + TIPA-16 mole PO (5 ppm) | 50 | 75 | 80 | 90 | 100 |
|  | 100 | 90 | 97 | 100 | 100 |
| MEAT (50 ppm) + TIPA-10 mole PO + TIPA 16 mole PO (5 ppm in 1:1 ratio) | 50 | 72 | 78 | ND | ND |
|  | 100 | 87 | 95 | ND | ND |
| MEAT (50 ppm) + TIPA-20 mole PO (5 ppm) | 50 | 79 | 75 | 90 | 95 |
|  | 100 | 95 | 90 | 100 | 100 |

The hydrogen sulphide scavenging efficiency of the present compositions comprising combination of MEAT (50% active) and amines of the present invention was also measured at temperature of 50° C. for different durations, i.e. at 1 hr., 2 hrs., 4 hrs., 6 hrs., and 48 hrs., and has been presented in Table VI. It has been found that the hydrogen sulphide scavenging efficiency of the MEAT surprising and unexpectedly improves on addition of amines of the present invention even after longer durations of time, thereby confirming the synergistic effect of the present compositions.

TABLE VI

| Additive | Dosage ppm as such | Efficiency, % (1 hr.) | Efficiency, % (2 hrs) | Efficiency, % (4 hrs) | Efficiency, % (6 hrs) | Efficiency, % (48 hrs) |
|---|---|---|---|---|---|---|
| MEA Triazine (50%) | 50 ppm | 20 | 25 | 30 | 35 | 50 |
| MEA Triazine (50%) + TIPA-PO 20 mole | 50 + 2.5 ppm | 50 | 75 | 85 | 90 | 99 |
| SR 1954 (MEAT-50, BKC80-5/water-45) | 50 ppm | 35 | 45 | 55 | 60 | 90 |

For the comparative purpose, the hydrogen sulphide scavenging efficiency of the compositions comprising combination of MEAT (50% active) and PPG and PEG of various molecular weights (as measured by GPC in Daltons), and prior art additive BKC (benzalkonium quaternary ammonium salt) was also measured at various temperatures, i.e. at room temperature (26° C.), and at 60° C., 80° C. and 100° C., and has been presented in Table VII. It has been found that the hydrogen sulphide scavenging efficiency of the MEAT improves, but very marginally on addition of PPG, PEG, prior art additive BKC, thereby confirming that the PPG and PEG do not have synergistic effect.

TABLE VII

| Composition (dosage in ppm) | Dosage (ppm) as such | % Efficiency (RT, 26° C.) | % Efficiency (60° C.) | % Efficiency (80° C.) | % Efficiency (100° C.) |
|---|---|---|---|---|---|
| Blank | — | — | — | — | — |
| MEAT | 50 | 25 | 15 | 11 | 5 |
|  | 100 | 50 | 40 | 20 | 15 |
|  | 200 | 65 | 50 | 30 | 20 |
|  | 300 | 75 | 70 | 60 | 45 |
| MEAT/PPG-400 (MEAT-50/PPG400-5) | 50 | 30 | 15 | 13 | 8 |
|  | 100 | 49 | 38 | 23 | 18 |
| MEAT/PPG-1000 (MEAT-50/PPG1000-5) | 50 | 26 | 18 | 15 | 10 |
|  | 100 | 49 | 40 | 25 | 20 |
| MEAT/PPG-2000 (MEAT-50/PPG2000-5) | 50 | 30 | 15 | 15 | 10 |
|  | 100 | 49 | 40 | 30 | 25 |
| MEAT/PPG-3000 (MEAT-50/PPG3000-5) | 50 | 28 | 20 | 20 | 15 |
|  | 100 | 51 | 43 | 35 | 30 |
| MEAT/PPG-4000 (MEAT-50/PPG4000-5) | 50 | 31 | 23 | 23 | 20 |
|  | 100 | 54 | 48 | 40 | 35 |

TABLE VII-continued

| Composition (dosage in ppm) | Dosage (ppm) as such | % Efficiency (RT, 26° C.) | % Efficiency (60° C.) | % Efficiency (80° C.) | % Efficiency (100° C.) |
| --- | --- | --- | --- | --- | --- |
| MEAT/PEG-200 | 50 | 28 | 18 | 10 | 10 |
| (MEAT-50/PEG200-5) | 100 | 50 | 44 | 20 | 15 |
| MEAT/PEG-400 | 50 | 25 | 18 | 15 | 10 |
| (MEAT-50/PEG400-5) | 100 | 48 | 46 | 20 | 20 |
| MEAT/PEG-600 | 50 | 35 | 21 | 15 | 10 |
| (MEAT-50/PEG600-5) | 100 | 58 | 49 | 18 | 23 |
| SR 1954 | 50 | 45 | 30 | 30 | 30 |
| (MEAT-50/BKC-5) | 100 | 80 | 60 | 50 | 45 |
|  | 200 | 99 | 70 | 65 | 60 |
|  | 300 | 100 | 80 | 80 | 70 |

The hydrogen sulphide scavenging efficiency of the present compositions comprising combination of MEAT (50% active) and amines of the present invention was also measured at temperature of 50° C. for duration of 15 min., and compared with diethyl amine (DEA, which contains "—OH" group, but is a secondary amine), trimethylamine (TEA), tetraethylenepentamine (TEPA, which is a secondary and mono amine, and does not contain —OH group), and has been presented in Table VIII. It has been found that the hydrogen sulphide scavenging efficiency of the MEAT surprising and unexpectedly improves on addition of amines of the present invention even after shorter durations of 15 mins., thereby confirming the synergistic effect of the present compositions.

For example, there is substantial improvement in the hydrogen sulphide scavenging efficiency at all dosages for composition comprising MEAT and TIPA, particularly at 700 ppm dosage the % efficiency for H2S scavenging improves from 70% to 95% and at 900 ppm dosage the improvement is from 77.5% to >99.5%. Same synergistic effect was found for the present compositions comprising MEAT and PO-TIPA. Similarly, there is substantial improvement at all dosages, particularly at 700 ppm dosage the % efficiency for H2S scavenging improves from 70% to 87.5%, and at 900 ppm dosage the improvement is from 77.5% to 95% for the present composition comprising MEAT and THEED.

On the contrary, the comparative composition comprising MEAT and DEA did not show improvement at all dosages. For example, at 700 ppm dosage the % efficiency for H2S scavenging improves very marginally from 70% to 72.5%, and at 900 ppm dosage there is no improvement. i.e. it remains at 77.5%.

Similarly, the another comparative composition comprising MEAT and TEA also did not show improvement at all dosages. For example, at 700 ppm dosage the % efficiency for H2S scavenging improves very marginally from 70% to 75%, and at 900 ppm dosage there is no improvement. i.e. it remains at 77.5%.

Similarly, the another comparative composition comprising MEAT and TEPA also did not show improvement at all dosage. For example, at 700 ppm dosage the % efficiency for H2S scavenging improves marginally from 70% to 75%, and at 900 ppm dosage also it improves marginally from 77.5% to 80%.

TABLE VIII

| Composition [MEAT + Amine] | Dosage (in ppm) [MEAT + Amine] | % Efficiency (at 50° C.) |
| --- | --- | --- |
| MEAT | 500 | 37.5 |
|  | 600 | 65.0 |
|  | 700 | 70.0 |
|  | 900 | 77.5 |
| MEAT + TIPA (Present Composition) | 500 + 25 | 55.0 |
|  | 600 + 30 | 90.0 |
|  | 700 + 35 | 95.0 |
|  | 900 + 45 | >99.5 |
| MEAT + TIPA-PO, 25 mole (Present Composition) | 500 + 25 | 98.9 |
|  | 600 + 30 | >99.95 |
|  | 700 + 35 | >99.95 |
|  | 900 + 45 | >99.95 |
| MEAT + TIPA-PO, 30 mole (Present Composition) | 500 + 25 | 99.1 |
|  | 600 + 30 | >99.95 |
|  | 700 + 35 | >99.95 |
|  | 900 + 45 | >99.95 |
| MEAT + THEED (Present Composition) | 500 + 25 | 47.5 |
|  | 600 + 30 | 75.0 |
|  | 700 + 35 | 87.5 |
|  | 900 + 45 | 95.0 |
| MEAT + DEA (Comparative Composition) | 500 + 25 | 40.0 |
|  | 600 + 30 | 67.5 |
|  | 700 + 35 | 72.5 |
|  | 900 + 45 | 77.5 |
| MEAT + TEA (Comparative Composition) | 500 + 25 | 42.5 |
|  | 600 + 30 | 67.5 |
|  | 700 + 35 | 75.0 |
|  | 900 + 45 | 77.5 |
| MEAT + TEPA Comparative Composition) | 500 + 25 | 45.0 |
|  | 600 + 30 | 70.0 |
|  | 700 + 35 | 75.0 |
|  | 900 + 45 | 80.0 |

The hydrogen sulphide scavenging efficiency of the present compositions comprising combination of MEAT (32% active) and amines of the present invention was also measured at temperature of 50° C. for duration of 15 min., and has been presented in Tables IX to XV. It has been found that the hydrogen sulphide scavenging efficiency of the MEAT surprisingly and unexpectedly improves on addition of amines of the present invention, thereby confirms the synergistic effect of the present compositions.

TABLE IX

| Dosage (in ppm) [MEAT + Amine] | MEAT + TIPA in 90:10 weight ratio |
| --- | --- |
| 500 + 17.5 | 75 |
| 600 + 21 | 82.5 |
| 700 + 24.5 | 89 |
| 900 + 31.5 | 91 |

The data in Table IX confirms that on addition of TIPA to MEAT, a synergistic effect (improvement in percent (%) hydrogen sulfide scavenging efficiency) is seen.

TABLE X

| Dosage (in ppm) [MEAT + Amine + Oxide derivative of NP] | MEAT + TIPA + 'NP-EO 40 mole' in 90:7:3 weight ratio | Dosage (in ppm) [MEAT + Amine + Oxide derivative of NP] | MEAT + TIPA + 'NP-EO 40 mole' in 90:5:5 weight ratio |
|---|---|---|---|
| 300 + 7.35 + 3.15 | 93 | 300 + 5.25 + 5.25 | 66.25 |
| 400 + 9.8 + 4.2 | 99.8 | 400 + 7 + 7 | 80 |
| 500 + 12.25 + 5.25 | >99.95 | 500 + 8.75 + 8.75 | 92.5 |
| 600 + 14.7 + 6.3 | | 600 + 10.5 + 10.5 | 99.2 |

The data in Table X confirms that on addition of (ethylene) oxide derivative of nonyl phenol (NP) to a combination of MEAT and TIPA, a synergistic effect (improvement in percent (%) hydrogen sulfide scavenging efficiency) is seen.

TABLE XIa

| Dosage (in ppm) [MEAT + Amine] | MEAT + 'TIPA-PO 30 mole' in 90:10 weight ratio | Dosage (in ppm) [MEAT + Amine + Oxide derivative of NP] | MEAT + 'TIPA-PO 30 mole' + 'NP-EO 20 mole' in 90:7:3 weight ratio | Dosage (in ppm) [MEAT + Amine + Oxide derivative of NP] | MEAT + 'TIPA-PO 30 mole' + 'NP-EO 20 mole' in 90:5:5 weight ratio |
|---|---|---|---|---|---|
| 500 + 17.5 | 91.2 | 300 + 7.35 + 3.15 | 72.7 | 300 + 5.25 + 5.25 | 72.5 |
| 600 + 21 | 99.6 | 400 + 9.8 + 4.2 | 87.5 | 400 + 7 + 7 | 87.5 |
| 700 + 24.5 | 99.95 | 500 + 12.25 + 5.25 | 99.9 | 500 + 8.75 + 8.75 | 98 |
| 900 + 31.5 | >99.95 | 600 + 14.7 + 6.3 | >99.95 | 600 + 10.5 + 10.5 | >99.95 |

The data in Table XIa confirms that on addition of TIPA-PO to MEAT, and on addition of (ethylene) oxide derivative of nonyl phenol (NP) to a combination of MEAT and TIPA-PO, a synergistic effect (improvement in percent (%) hydrogen sulfide scavenging efficiency) is seen.

TABLE XIb

| Dosage (in ppm of composition) | MEAT | MEAT + TI16P in 90:10 weight ratio | MEAT + TI20P in 90:10 weight ratio | MEAT + TI25P in 90:10 weight ratio | MEAT + TI30P in 90:10 weight ratio |
|---|---|---|---|---|---|
| 500 | 45.5 | 81.8 | 90.9 | 90.0 | 91.2 |
| 600 | 72.7 | ND | 99.1 | 99.5 | 99.6 |
| 700 | 77.3 | 97.7 | 99.8 | 99.95 | 99.95 |
| 900 | 84.1 | 99.5 | 99.95 | >99.95 | >99.95 |

The data in Table XIb confirms that on addition of TIPA-PO to MEAT, a synergistic effect (improvement in percent (%) hydrogen sulfide scavenging efficiency) is seen.

TABLE XII

| Dosage (in ppm) [MEAT + Amine] | MEAT + 'TIPA-PO 30 mole' in 90:10 weight ratio | Dosage (in ppm) [MEAT + Amine + Oxide derivative of NP] | MEAT + 'TIPA-PO 30 mole' + 'NP-PO 40 mole' in 90:7:3 wt. ratio | Dosage (in ppm) [MEAT + Amine + Oxide derivative of NP] | MEAT + 'TIPA-PO 30 mole' + 'NP-PO 40 mole' in 90:5:5 wt. ratio |
|---|---|---|---|---|---|
| 500 + 17.5 | 91.2 | 300 + 7.35 + 3.15 | 67.5 | 300 + 5.25 + 5.25 | 67.5 |
| 600 + 21 | 99.6 | 400 + 9.8 + 4.2 | 82.5 | 400 + 7 + 7 | 82.5 |

TABLE XII-continued

| Dosage (in ppm) [MEAT + Amine] | MEAT + 'TIPA-PO 30 mole' in 90:10 weight ratio | Dosage (in ppm) [MEAT + Amine + Oxide derivative of NP] | MEAT + 'TIPA-PO 30 mole' + 'NP-PO 40 mole' in 90:7:3 wt. ratio | Dosage (in ppm) [MEAT + Amine + Oxide derivative of NP] | MEAT + 'TIPA-PO 30 mole' + 'NP-PO 40 mole' in 90:5:5 wt. ratio |
|---|---|---|---|---|---|
| 700 + 24.5 | 99.95 | 500 + 12.25 + 5.25 | 95 | 500 + 8.75 + 8.75 | 94 |
| 900 + 31.5 | >99.95 | 600 + 14.7 + 6.3 | >99.95 | 600 + 10.5 + 10.5 | 99.8 |

The data in Table XII confirms that on addition of TIPA-PO to MEAT, and on addition of (propylene) oxide derivative of nonyl phenol (NP) to a combination of MEAT and TIPA-PO, a synergistic effect (improvement in percent (%) hydrogen sulfide scavenging efficiency) is seen.

TABLE XIII

| Dosage (in ppm) [MEAT + Amine + Oxide derivative of NP] | MEAT + 'TIPA-EO 26 mole' + 'NP-EO 40 mole' in 90:7:3 weight ratio | Dosage (in ppm) [MEAT + Amine + Oxide derivative of NP] | MEAT + 'TIPA-EO 26 mole' + 'NP-EO 40 mole' in 90:5:5 weight ratio |
|---|---|---|---|
| 300 + 7.35 + 3.15 | 67.5 | 300 + 5.25 + 5.25 | 66.25 |
| 400 + 9.8 + 4.2 | 82.5 | 400 + 7 + 7 | 81.25 |
| 500 + 12.25 + 5.25 | 94.5 | 500 + 8.75 + 8.75 | 93.75 |
| 600 + 14.7 + 6.3 | 99.9 | 600 + 10.5 + 10.5 | 98 |

The data in Table XIII confirms that on addition of (ethylene) oxide derivative of nonyl phenol (NP) to combination of MEAT and TIPA-EO, a synergistic effect (improvement in percent (%) hydrogen sulfide scavenging efficiency) is seen.

TABLE XIV

| Dosage (in ppm) [MEAT + Amine] | MEAT + 'EDA-PO 16 mole' in 90:10 weight ratio | Dosage (in ppm) [MEAT + Amine + Oxide derivative of NP] | MEAT + 'EDA-PO 16 mole' + 'NP-EO 40 mole' in 90:7:3 wt. ratio |
|---|---|---|---|
| 500 + 17.5 | 92 | 300 + 7.35 + 3.15 | 75 |
| 600 + 21 | 94.1 | 400 + 9.8 + 4.2 | 92 |
| 700 + 24.5 | 99.5 | 500 + 12.25 + 5.25 | 99.9 |
| 900 + 31.5 | >99.95 | 600 + 14.7 + 6.3 | >99.95 |

The data in Table XIV confirms that on addition of EDA-PO to MEAT, and on addition of (ethylene) oxide derivative of nonyl phenol (NP) to combination of MEAT and EDA-PO, a synergistic effect (improvement in percent (%) hydrogen sulfide scavenging efficiency) is seen.

TABLE XV

| Dosage (in ppm) [MEAT + Amine + Oxide derivative of NP] | MEAT + EDA-PO 16 mole + NP-PO 40 mole in 90:7:3 weight ratio | Dosage (in ppm) [MEAT + Amine + Oxide derivative of NP] | MEAT + EDA-PO 16 mole + NP-PO 40 mole in 90:5:5 weight ratio |
|---|---|---|---|
| 300 + 7.35 + 3.15 | 80 | 300 + 5.25 + 5.25 | 82.5 |
| 400 + 9.8 + 4.2 | 95 | 400 + 7 + 7 | 96.5 |
| 500 + 12.25 + 5.25 | 99.9 | 500 + 8.75 + 8.75 | 99.9 |
| 600 + 14.7 + 6.3 | >99.95 | 600 + 10.5 + 10.5 | >99.95 |

The data in Table XV confirms that on addition of EDA-PO and NP-PO to MEAT, a synergistic effect (improvement in percent (%) hydrogen sulfide scavenging efficiency) is seen.

The foregoing examples confirm synergistic effects, i.e. surprising and unexpected effects of the present invention over the prior art.

Therefore, the foregoing experiments confirm that nitrogen based compositions are capable of scavenging $H_2S$. However, when the present composition comprising a combination of nitrogen based $H_2S$ scavengers and one or more aliphatic tertiary amine is used, the $H_2S$ scavenging efficiency of the nitrogen based $H_2S$ scavengers is, surprisingly and unexpectedly, substantially increased confirming synergistic effect of the scavenging additive composition of the present invention.

The above experimental findings confirm surprising, and unexpected technical effects and advantages, and synergistic property of the presently provided hydrogen sulfide scavenging additive compositions.

The above findings also confirm that compositions of the present invention have technical advantages and surprising effects over the prior art and comparative additives and compositions.

It may be noted that the present invention has been described with the help of foregoing examples, which are not intended to limit scope of the present invention, but are only illustrative.

Furthermore, as amount of the prior art additive (i.e. triazine) has been substantially reduced to achieve desired scavenging efficiency, the present compositions are more economical and environmental friendly.

It may be noted that the term "about" as employed herein is not intended to enlarge scope of claimed invention, but has been incorporated only to include permissible experimental errors of the field of the present invention.

The invention claimed is:

1. A hydrogen sulfide scavenging additive composition for scavenging hydrogen sulfide in hydrocarbon comprising sulfur containing compounds, wherein said additive composition consists of a combination of:

(A) at least one nitrogen based hydrogen sulfide scavenger; and
(B) at least one aliphatic tertiary amine,
wherein the nitrogen based hydrogen sulfide scavenger comprises triazine based hydrogen sulfide scavenger; and
wherein the aliphatic tertiary amine comprises tri-isopropanolamine (TIPA), N,N,N',N'-Tetrakis (2-hydroxyethyl) ethylene-diamine (THEED), ethylene oxide (EO) derivative of TIPA (EO-TIPA), propylene oxide (PO) derivative of TIPA (PO-TIPA), ethylene oxide (EO) derivative of ethylene diamine (EO-EDA), propylene oxide (PO) derivative of ethylene diamine (PO-EDA), or a mixture thereof; and
wherein the composition does not comprise:
a) monoethanol amine (MEA);
b) diethanol amine (DEA); and
c) triethanol amine (TEA).

2. The additive composition as claimed in claim 1, wherein the triazine based hydrogen sulfide scavenger comprises mono-ethanolamine triazine (MEAT) based hydrogen sulfide scavenger.

3. The additive composition as claimed in claim 1, wherein the composition further comprises oxide derivative of nonyl phenol (NP).

4. The additive composition as claimed in claim 3, wherein the oxide derivative of nonyl phenol comprises an ethylene oxide (EO) derivative of nonyl phenol (EO-NP) or propylene oxide (PO) derivative of nonyl phenol (PO-NP), or a mixture thereof.

5. The additive composition as claimed in claim 1, wherein the hydrocarbon comprising sulfur containing compounds comprises hydrocarbon stream selected from the group comprising crude oil, fuel oil, sour gas, asphalts and refined products.

6. The additive composition as claimed in claim 1, wherein the sulfur containing compounds comprise hydrogen sulfide containing compounds, mercaptans, or a mixture thereof.

7. A composition comprising:
(a) a hydrocarbon; and
(b) a hydrogen sulfide scavenging additive composition;
wherein the hydrogen sulfide scavenging additive composition consists of a combination of:
(A) at least one nitrogen based hydrogen sulfide scavenger; and
(B) at least one aliphatic tertiary amine,
wherein the hydrocarbon comprises sulfur containing compounds;
wherein the nitrogen based hydrogen sulfide scavenger comprises triazine based hydrogen sulfide scavenger; and
wherein the aliphatic tertiary amine is as claimed in claim 1.

8. The composition as claimed in claim 7, wherein the triazine based hydrogen sulfide scavenger comprises mono-ethanolamine triazine (MEAT) based hydrogen sulfide scavenger.

9. The composition as claimed in claim 7, wherein the composition further comprises oxide derivative of nonyl phenol (NP).

10. The composition as claimed in claim 9, wherein the oxide derivative of nonyl phenol comprises an ethylene oxide (EO) derivative of nonyl phenol (EO-NP) or propylene oxide (PO) derivative of nonyl phenol (PO-NP), or a mixture thereof.

11. A method for scavenging hydrogen sulphide in hydrocarbon comprising sulfur containing compounds, wherein the method comprises contacting the hydrocarbon with the hydrogen sulfide scavenging additive composition, wherein the hydrogen sulfide scavenging additive composition is as claimed in claim 1.

12. A method of using the hydrogen sulfide scavenging additive composition for scavenging hydrogen sulphide in hydrocarbon comprising sulfur containing compounds, wherein the method comprises adding to the hydrocarbon the hydrogen sulfide scavenging additive composition as claimed in claim 1.

* * * * *